United States Patent [19]

O'Meara, Jr. et al.

[11] Patent Number: 4,567,373
[45] Date of Patent: Jan. 28, 1986

[54] CENTRIFUGAL ANALYZER

[75] Inventors: Joseph D. O'Meara, Jr.; Herbert H. Yuan; William O. Lease; Robert G. Stapleton, all of Houston, Tex.

[73] Assignee: Shell Oil Company, Houston, Tex.

[21] Appl. No.: 435,430

[22] Filed: Oct. 20, 1982

[51] Int. Cl.⁴ .............................................. G01H 15/06
[52] U.S. Cl. ...................................... 250/573; 356/427
[58] Field of Search ............... 250/573, 576, 577, 564, 250/575; 356/436, 440, 441, 442, 427, 70, 426, 428, 23; 73/61.1 R, 57

[56] References Cited

U.S. PATENT DOCUMENTS

| | | | |
|---|---|---|---|
| 3,582,218 | 6/1971 | Anderson | 356/427 |
| 3,807,874 | 4/1974 | Gropper | 356/436 |
| 3,900,266 | 8/1975 | Takahashi et al. | 356/442 |
| 3,966,332 | 6/1976 | Knapp et al. | 356/427 |
| 3,999,868 | 12/1976 | Sanz et al. | 356/427 |
| 4,221,125 | 9/1980 | Oliver et al. | 73/61.1 R |
| 4,234,799 | 11/1980 | Okumura | 250/576 |
| 4,265,535 | 5/1981 | Pitt | 250/575 |
| 4,434,650 | 3/1984 | Perry et al. | 73/61.1 R |

OTHER PUBLICATIONS

Archives of Biochemistry and Biophysics 158, 864–888 (1973), Optical Multichannel Analyzer as a Scanner for the Ultracentrifuge, by E. G. Richards and D. Rockholt.

Primary Examiner—David C. Nelms
Assistant Examiner—J. Gatto

[57] ABSTRACT

A centrifugal analyzer comprising a container adapted for holding a sample, a centrifuge having a rotor which holds the container, a source of electromagnetic energy and an array of photodiode means. The source is positioned such that at least a portion of the electromagnetic energy provided thereby impinges on the container, and the array of photodiode means is positioned such that at least a portion of the electromagnetic energy that impinges on the container is sensed by the array.

11 Claims, 5 Drawing Figures

CENTRIFUGAL ANALYZER

BACKGROUND OF THE INVENTION

This invention relates to a system for monitoring a sample during centrifugation and, more particularly, to a system for monitoring the fluid volumes collected as a function of time during the centrifugation of a sample of core material that has been removed from the borehole of an oil well.

The use of a centrifuge to measure properties, such as relative permeabilties and capillary pressures, of core material is well known to prior art workers in the petrophysical measurements of core material. In general, a fluid saturated core sample is rotated, and the fluids that are displaced from the sample are collected in an attached collection tube. The most difficult aspect of the measurement is monitoring the fluid volumes as a function of time; these measurements are generally performed by a technician who observes and records the fluid levels at predetermined intervals. However, since test runs may take several days and fluid changes may occur very rapidly during the first portion of the test, the prior art method of manually monitoring the process is tedious and may result in poor accuracy. In addition, the prior art has monitored the fluid production by programming a camera to take pictures at preset times. Again, this process is a tedious one, since the developed film must be analyzed manually to gather the appropriate data. Another drawback of this method is that if a malfunction occurs during the run, which can last up to a week, the malfunction often is not detected until the film has been developed; hence, corrective action is usually impossible. Moreoever, the number of data points that can be collected by this method is limited to the number of exposures available on the film.

Therefore, it is an object of the present invention to provide a system that automatically monitors a sample during centrifugation and provides a plurality of data points indicative of the characteristic of such sample that is being tested by the centrifugation.

SUMMARY OF THE INVENTION

In accordance with the present invention there is provided a centrifugal analyzer comprising: a container adapted for holding a sample, a centrifuge having a rotor which holds the container, a source of electromagnetic energy and an array of photodiode means. The electromagnetic energy source is positioned such that at least a portion of the electromagnetic energy provided thereby impinges on the container, and the array of photodiode means is positioned such that at least a portion of the electromagnetic energy that impinges on the container is sensed by the array.

In addition, the present invention provides a method of centrifugally analyzing a sample comprising the steps of: rotating the sample; illuminating the sample with electromagnetic energy; positioning an array of photodiode means such that at least a portion of the electromagnetic energy that illuminates the sample impinges on the array; and sensing the amount of electromagnetic energy that impinges on each of the photodiode means in the array.

The present invention utilizes a photodiode array to image the position of the fluid or fluids in a rotating collection tube. The array is mounted in a suitable camera and aligned parallel to the major axis of the liquid collection tube. In the preferred embodiment, the collection tube is intermittently illuminated by a strobe, and the light impinging on each photodiode is converted to an electric signal which can be displayed, stored and analyzed by suitable electronic equipment. The strobe can be positioned so that light reflected from the collection tube impinges on the photodiode array, or, preferably, the strobe can be positioned so that light transmitted through the collection tube impinges on the photodiode array. It has been found that transmitted light provides a sharper demarcation between two or more fluids in the collection tube, thus facilitating the monitoring of a plurality of fluids produced by the sample during centrifugation. Other types of electromagnetic energy, such as X rays and gamma rays, can be used with the system of the present invention. The wavelength response of the photodiode array can be extended to detect the X rays or gamma rays by placing, for example, phosphor on the array. The radiation impinging on the phosphor causes the phosphor to emit light which is sensed by the photodiode array. In an alternative embodiment the source of electromagnetic energy can be a constant source rather than a strobe or intermittent source, and the photodiode array can be intermittently exposed by a shutter on the camera in which it is mounted or by other suitable means.

Preferably, the collection tube has a precision bore and a square cross section. Prior art cylindrical collection tubes generally act as a lens and, thus, concentrate all of the strobe light in a narrow band along the tube's major axis. This lens effect decreases the area over which the photodiode array can gather useful data and, therefore, requires that the strobe timing be precise in order to obtain a usable image. The precision bore allows the volume of fluid collected to be monitored as a direct function of the number of photodiodes spanned. The demarcation between two or more fluids in the collection tube can be enhanced by placing a light diffracting material, that floats on the interface of interest, in the collection tube before starting the centrifuging process.

The system of the present invention is particularly adapted to monitoring the fluid volumes collected as a function of time during the centrifugation of a sample of core material that has been removed from the borehole of an oil well. The system minimizes manpower needs and provides a plurality of data points sensed at predetermined intervals throughout the run. If desired, a computer can be employed to analyze the data in real time to provide an output indicative of the amount of fluid or fluids produced by the core sample during centrifugation. However, it should be noted that although the system is particularly adapted to monitoring core samples the system can monitor the level of any fluid or fluids during centrifugation. In addition, the system can be used to monitor a sample that contains both a fluid and a solid suspended therein so that the photodiode array images the relative amounts or levels of the fluid and sediment in the rotating collection tube. Still further, the present invention can be utilized to monitor the concentration gradient of a sample by imaging the relative shades throughout the sample as it is rotating. Other objectives, advantages and applications of the present invention will be made apparent by the following detailed description of the preferred embodiments of the present invention.

DETAILED DESCRIPTION OF THE PREFERRED EMBODIMENTS

Figure 1:
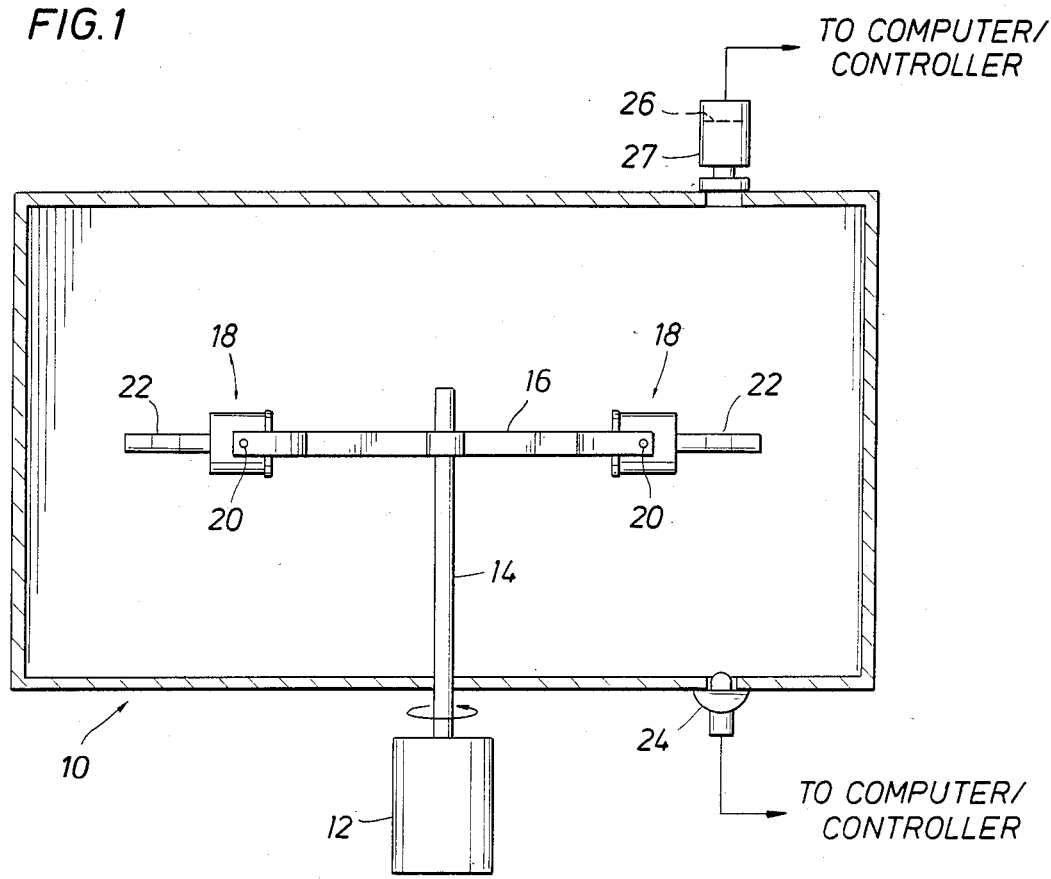
FIG. 1 is a partial diagrammatic view in side elevation of the centrifugal analyzer of the present invention.

Referring to FIG. 1, a centrifuge 10, such as model DPR-6000 available from International Equipment Co., Needham Heights, Mass., consists of a motor 12 which drives a shaft 14; shaft 14 is connected to rotor 16 which holds sample holders 18 by any convenient means, such as pins 20. Sample holders 18 have a transparent collection tube 22 for collecting fluids displaced from the sample during centrifugation. A stroboscope or strobe 24, such as the strobotac electronic stroboscope manufactured by Genrad of Concord, Mass., is positioned so that the light emitted therefrom impinges on one of collection tubes 22. A photodiode array 26 is positioned on the opposite side of collection tube 22 so that at least a portion of the light rays from strobe 24 that pass through collection tube 22 will impinge upon photodiode array 26. It should be noted that both strobe 24 and photodiode array 26 can be positioned on the same side of collection tube 22 such that reflected light rather than transmitted light impinges on photodiode array 26. Photodiode array 26 can comprise, for example, a line of 1024 light sensitive photodiodes, each of which is 13 micrometers by 25 micrometers in size and are spaced 25 micrometers apart, such as the RL 1024C photodiode array available from EG&G Reticon of Sunnyvale, Calif. However, photodiode array 26 can be an n by m array where n and m can be any suitable size. Photodiode array 26 is mounted in camera 27, such as the LC 110U1024-1 line scan camera available from EG&G Reticon. Camera 27 is mounted on centrifuge 10 such that the only light that enters camera 27 is the light provided by strobe 24 and such that photodiode array 26 is aligned parallel to the major axis of collection tube 22. Both strobe 24 and photodiode array 26 are connected to a controller, as is explained in detail hereinbelow. Centrifuge 10 can be provided with suitable means for indexing and aligning sample holders 18, such as index marks, infrared diode/phototransistor combinations and the like, as is known in the art.

Figure 2:
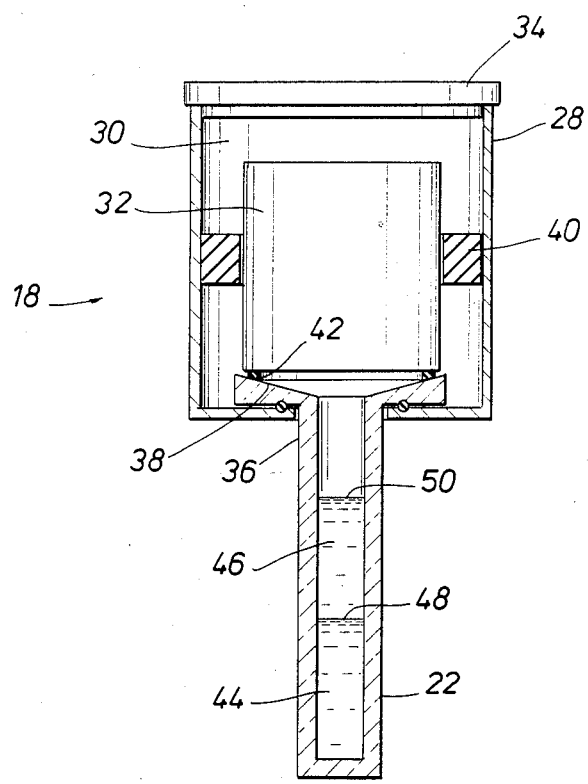
FIG. 2 is a detailed view in side elevation of the sample holder incorporated in the centrifugal analyzer shown in FIG. 1.

FIG. 2 illustrates a detailed view of one embodiment of sample holder 18 which is adapted for holding a core sample from a downhole core of an oil well; this example is served by way of illustration and not limitation, since the apparatus of the present invention can be employed to analyze various solids, mixtures and fluids, for example, human blood. Sample holder 18 comprises a core housing 28 which has a chamber 30 that is suitably sized to accommodate core sample 32. Core housing 28 is provided with lid 34 to facilitate loading and unloading of core sample 32. Collection tube 22 is positioned in aperture 36 of core housing 28 which is located on the side of core housing 28 that is opposite lid 34. The open portion of collection tube 22 that is located adjacent to core sample 32 is inclined as indicated by numeral 38. Preferably, collection tube 22 has a precision bore and a square cross section. A spacer ring 40 is positioned around core sample 32, and a support ring 42 is positioned between core sample 32 and inclined portion 38 of collection tube 22. Spacer ring 40 and support ring 42 can be made of any suitable resilient material. The water and oil that are produced during centrifugation of a water-oil saturated core sample are indicated by numerals 44 and 46, respectively. Preferably, light diffracting materials, that float on the oil-water interface and the oil-air interface, are added to collection tube 22 prior to starting the test. The light diffracting material for floating on the oil-water interface and the oil-water interface itself are indicated generally by numeral 48. Light diffracting material 48 can be, for example, a thin film of polyethylene having a density of 0.91 grams per cubic centimeter. Similarly, the light diffracting material for floating on the oil-air interface and the oil-air interface itself are indicated generally by numeral 50. Cork dust is an example of a material suitable for use as light diffracting material 50.

Figure 3:
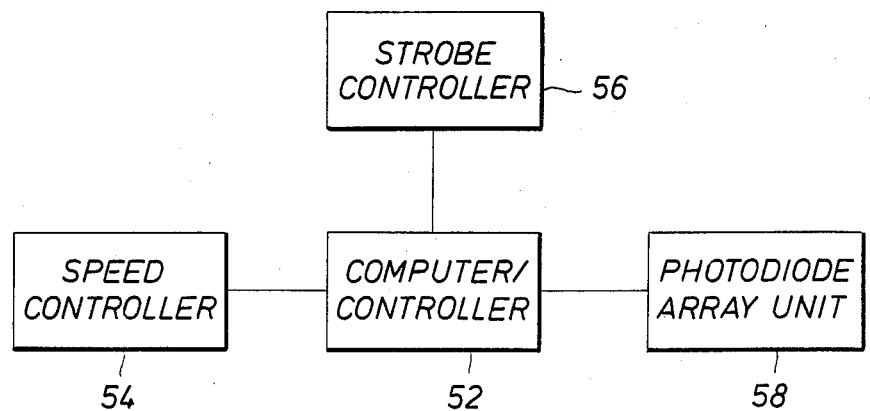
FIG. 3 is a schematic block diagram showing a control system according to the invention in a microcomputer based system.

A suitable control system for implementing the centrifuge system of the present invention is disclosed in FIG. 3. Computer/controller 52 is connected to speed controller 54, strobe controller 56 and photodiode array unit 58. Computer/controller 52 can be a microcomputer which performs all of the control functions described hereinbelow, as well as providing data storage and real time processing of the information provided by photodiode array unit 58. If desired, the various control functions can be performed by a separate controller circuit which directs the output from photodiode array unit 58 to a microcomputer which can perform the data storage and processing. Still further, a strip chart or other storage device can be used in place of the microcomputer to store the desired data. Speed controller 54 controls the speed at which rotor 16 of centrifuge 10 of FIG. 1 is rotated. Computer/controller 52 provides a signal to speed controller 54 which indicates the desired rotor speed. Generally, for relative permeability experiments the rotor is run at a high speed, for example, 2000-4000 revolutions per minute, to counteract capillary forces, and liquid production is monitored as a function of time. For capillary pressure experiments, generally, the speed of the rotor is increased in predetermined steps, and the liquid production is measured at each speed after capillary equilibrium has been reached. Strobe controller 56, which can be the control circuitry of the aforesaid strobotac electronic stroboscope manufactured by Genrad, provides a predetermined number of strobe flashes in response to a control signal from computer/controller 52. It has been found that two strobes positioned side by side with the light producing elements thereof being covered by a sand-blasted Plexiglas member or the like diffuses the light and provides a uniform source of light.

Photodiode array unit 58 consists of a photodiode array and associated electronic circuitry mounted in a suitable camera, such as described hereinabove in reference to photodiode array 26 and camera 27 in FIG. 1. Each of the photodiodes in the array is connected in parallel with a capacitor which is charged to a predetermined saturation charge. This charge is leaked off by a current generated when light impinges on the photodiode. The remaining charge and, thus, the voltage across the capacitor is proportional to the amount of light striking the respective photodiode during a fixed exposure time. The photodiodes are scanned by a digital shift register which causes the voltage across the respective capacitors to be sent to a common output line. The capacitor is then refreshed to its original saturation charge, and the shift register moves on to the next photodiode in the array. Before computer/controller 52 requests a reading, the photodiodes are constantly being scanned and refreshed at a frequency determined by computer/controller 52. When computer/controller 52 determines that it is time to collect a data sample, it waits until the last scan to be completed so that each of the photodiodes is in a refreshed state. When computer/controller 52 determines that the last photodiode has been scanned and refreshed, it stops the scanning process and signals strobe controller 56 to provide the predetermined number of flashes to the appropriate collection tube. When computer/controller 52 determines that the collection tube has been strobed with the predetermined number of flashes, it signals photodiode array unit 58 to restart the scanning process. It should be noted that the only light that has been seen by the photodiode array is the light provided by the strobe flashes. The output signal provided by each photodiode and capacitor combination is provided to the common output line by the shift register. The common output line is connected to an analog-to-digital converter in computer/controller 52. The respective analog voltages are converted to equivalent digital signals and stored and/or processed by computer/controller 52. The scanning and refreshing cycle is then repeated, as described above, until the juncture at which the next data point is to be collected. If desired, a visual display of the output, such as that illustrated in FIG. 4, can be provided on a television monitor immediately after the array has been scanned.

Figure 4:
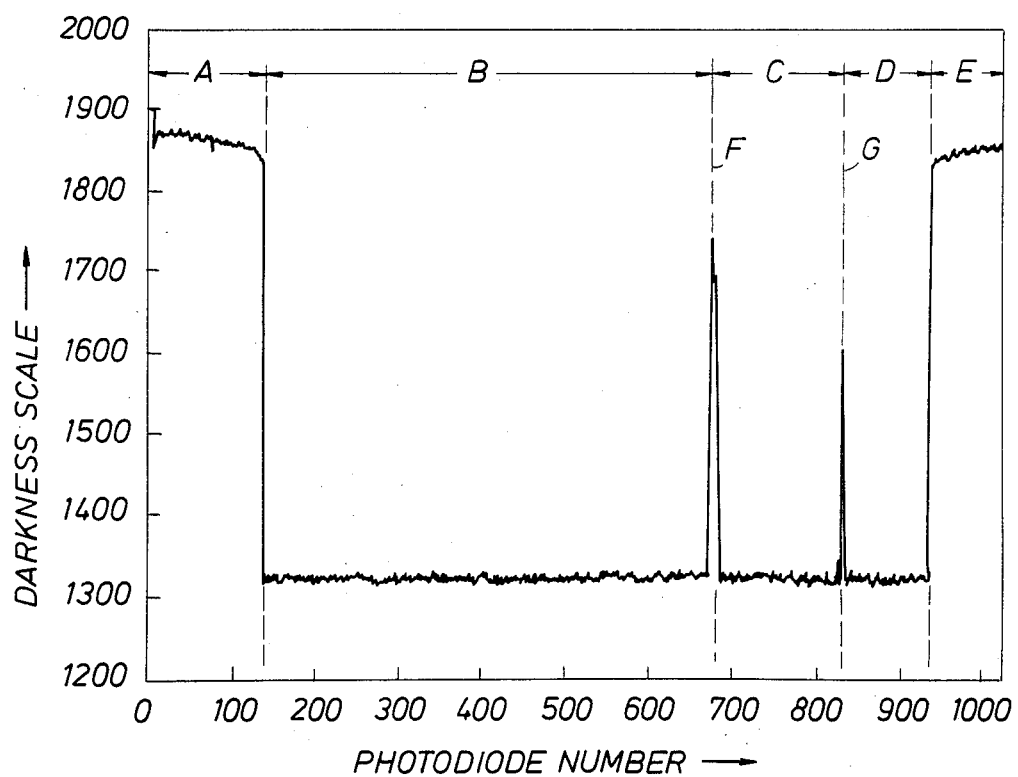
FIG. 4 illustrates a typical plot of the data obtained by the present invention.

FIG. 4 illustrates a typical plot of the output data from photodiode array unit 58 of FIG. 3 for a water-oil saturated core sample. High numbers on the vertical axis indicate photodiodes which receive very little light, and low numbers indicate relatively more light. The horizontal axis identifies the photodiodes in the array. The end of the collection tube which is farthest from the rotation axis shows up as the dark area which has been labeled "A", and the end of the collection tube that is closest to the rotation axis shows up as the dark area which has been labeled "E". The water that has been collected in the collection tube during centrifugation appears as the first dip or valley on the left hand side of the plot which has been labeled "B". The oil that has been collected in the collection tube from the core sample during centrifugation is indicated by the second dip or valley from the left hand side of the plot which has been labeled "C". The air or gas in the collection tube is indicated by the portion of the plot labeled "D". Starting from the left hand side of the plot, the first major peak which has been labeled "F" represents the water-oil interface, and the next major peak which has been labeled "G" represents the oil-air interface. As stated hereinabove, the data plotted in FIG. 4 can be recorded on a strip chart recorder, stored on a disc until the end of the experiment and then analyzed by a computer program, or analyzed by a computer program as it is being gathered. Generally, the reason for subjecting the core sample to centrifugation is to determine the amount of oil and water produced as a function of time. Therefore, since only two numbers have to be stored for each juncture, rather than the data point for each photodiode, computer analysis of the data while it is being gathered is generally preferred.

Figure 5:
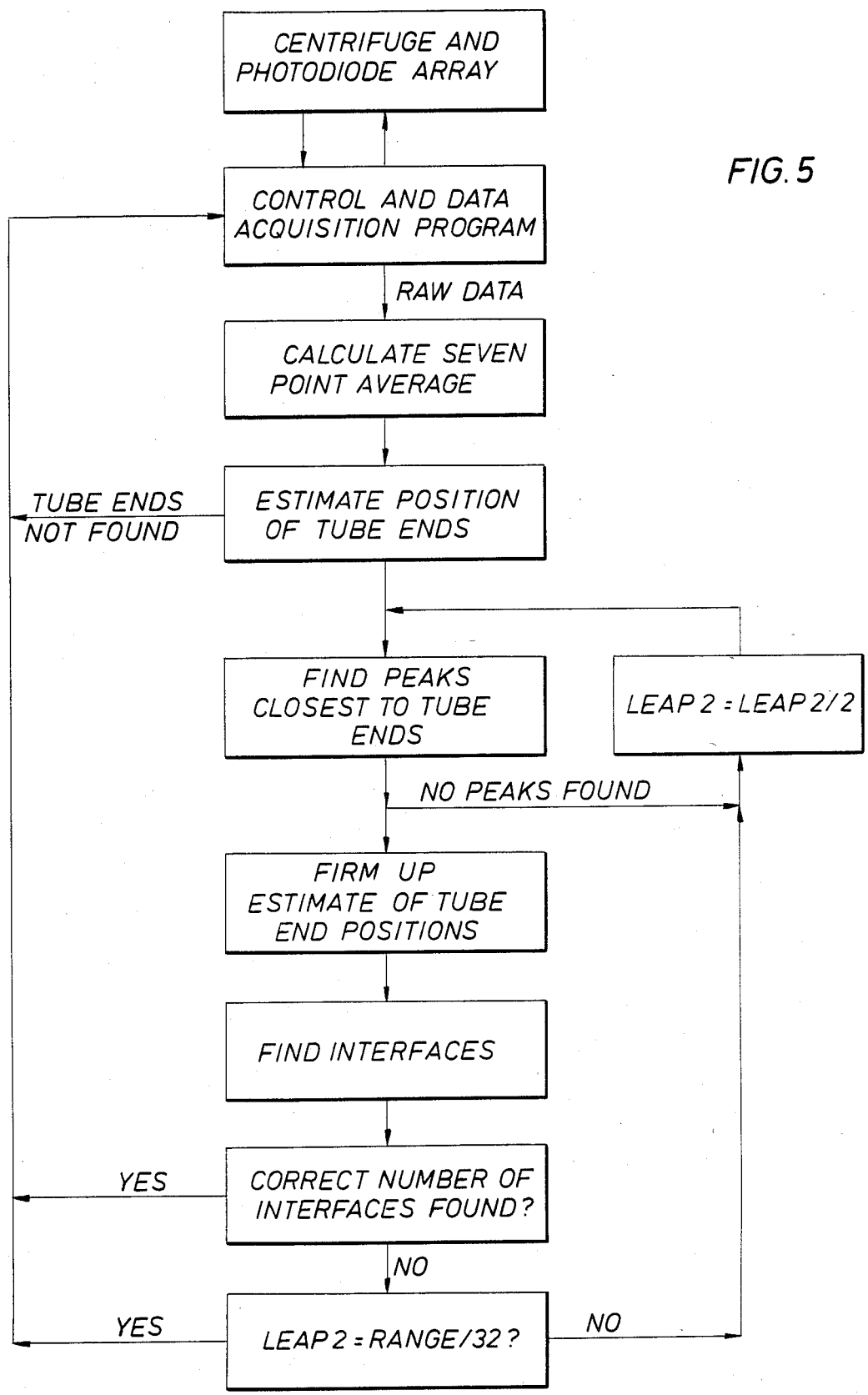
FIG. 5 is a flow chart illustrating a preferred method of determining the interfaces between fluids removed from the sample by centrifuging.

To determine the amount of liquid or liquids produced from the sample during centrifugation, computer/controller 52 of FIG. 3 implements a program which first searches for the ends of the collection tube and then finds the highest peak or peaks between the ends. For example, in the case where the experiment involves only one liquid being displaced by air, the liquid-air interface is located at the position of the highest peak. Calculating the positions of the tube ends not only narrows the search for the peak or peaks, but also monitors the movement of the ends caused by the vibrations of the rotary shaft of the centrifuge. FIG. 5 illustrates an abbreviated flow chart for the identification method described hereinbelow in detail. It should be noted that the method described herein pertains to a sample that contains transparent oil and water. If desired, the program can be modified to identify other interfaces, for example, opaque (crude) oil-fluid interfaces.

The raw data received from the respective photodiodes is smoothed or averaged before the program attempts to identify the ends of the collection tube. Using the smoothed data prevents misidentifying the end of the tubes as a result of spurious data and results in only a small loss of resolution in the search for the ends. The raw data is smoothed by using a seven point average with the Ith raw data point being transformed into the sum of itself with the three data points preceding and three data points following. This average can be expressed as:

$$ARRAY(I) = RAWDAT(I-3) + RAWDAT(I-2) + RAWDAT(I-1) + RAWDAT(I) + RAWDAT(I+1) + RAWDAT(I+2) + RAWDAT(I+3) \quad (1)$$

where:
ARRAY(I) is the seven point average of the raw data for I equal to 1 through X with X being the last photodiode in the array, and
RAWDAT(I) is the raw photodiode data for photodiodes from I to X. If desired, a true average can be obtained by dividing the right hand side of equation (1) by 7; however, division is a time consuming operation in a computer and an average such as that presented by equation (1) presents no problem provided that the computer has sufficient space to store the numbers generated.

Referring to FIG. 4, the tube ends are located by starting from either the far right or far left, moving toward the center and locating large drops in the level of the data. It has been found that by placing the camera in a predetermined location and using a predetermined lens or lenses, the collection tube is always located between certain photodiodes in the array. Therefore, the user can take advantage of this knowledge and specify that the search take place over the following range of ARRAY(I): $INFO(1) \leq I \leq INFO(2)$. The program calculates INFO(3) and INFO(4), the minimum and maximum values of ARRAY(I) for $INFO(1) \leq I \leq INFO(2)$, and $RANGE = INFO(4) - INFO(3)$. The local maximum, MAX1, is initially set equal to ARRAY(INFO(1)). I is incremented, and for each new ARRAY(I) the local maximum is updated and the program checked to determine if a drop such that MAX1−LEAP1>AR- RAY(I) has occurred. LEAP1 is the threshold for determining when a drop of significant size has occurred. Obviously, LEAP1 must be larger than the noise level of ARRAY(I) and should be smaller than the full range of ARRAY(I). It has been found that choosing LEAP1 as approximately one-fourth of the full range is quite adequate; therefore, LEAP1 is defined as LEAP1 =RANGE/4. Returning to the search for a significant drop in the level of the data as an indication of the end of the collection tube, IDIP1 is set equal to the value of I where this drop occurs. The other end of the tube is found by beginning the search at I=INFO(2) and following the procedure described above, except that I is now decremented. IDIP2 denotes the position where this dip occurs. If the program does not find two tube ends such as in the case when the camera does not have both ends within its field of view or if INFO(1) and INFO(2) are chosen too close together, the program is terminated before it begins searching for the fluid interfaces.

The next step in the program is to identify the peaks which characterize the interfaces and to firm up the estimate of where the tube ends occur. It has been found that a search of the raw data for the peaks indicative of the interfaces provides the highest degree of resolution. However, spurious data can lead to misidentification of the interfaces, so, as with the search for the tube ends, averaged data is preferred. The search for the peaks is performed between I=IDIP1 and IDIP2 for peaks of size greater than LEAP2 where LEAP2 is equal to RANGE/4. If this search fails to discover at least two peaks, LEAP2 is decreased by a factor of 2 and the search is repeated. With further failure to find two peaks, the search is repeated twice more with LEAP2 reaching a minimum equal to RANGE/32. After this fourth iteration, the search is abandoned to ensure against performing infinite program loops on the receipt of bad data. To determine the first significant peak in the neighborhood of the tube end in the vicinity I=IDIP1, the local minimum, MIN1 is initially set equal to RAWDAT(IDIP1), I is incremented, the local minimum is updated for each new RAWDAT(I) and the program checks for a leap upward in the data such that RAWDAT(I) is greater than LEAP2+MIN1. IUP1 is set equal to I when this leap is detected; this leap is due to the incline leading to the peak nearest the tube end.

Once this incline is detected, the estimate of the position of the nearby tube end is firmed up. Each time MIN1 is updated in the above search, the position at which the new local minimum occurs is stored. Once IUP1 is determined, a search is begun by starting at this position and decrementing I until a leap upward is found such that ARRAY(I) is greater than LEAP1+MIN1. The position of this leap upward at I=ITEMP also signals the presence of the same tube end indicated by the drop at I=IDIP1. If the transition from the tube end to the zone containing fluid occurred over just one photodiode, then IDIP1 is equal to ITEMP. However, this transition usually occurs over several photodiodes; therefore, the position of the tube end is defined as I=IDIP1+ITEMP)/2. This value of I is then stored. The process of searching for the end of the tube and the position of the incline to the nearest peak is repeated for I starting at INFO(2), except that the step of incrementing I in the above description corresponds to decrementing it in this portion of the search. The net result is that the position of the tube end near I=INFO(2) is stored, and the position of the incline leading to the second peak is labeled IUP2.

At this point, the range of I over which the search for the fluid interfaces will be conducted has been narrowed to IUP1 I≦IUP2. If IUP1 is greater than IUP2, it will be impossible to find any interfaces. In this case, the search enters the next iteration for LEAP2. If LEAP2 already equals RANGE/32, the search is terminated. Normally, however, IUP2 is greater than or equal to IUP1, in which case at least one peak will be found between the tube ends. On completing the search for each iteration, the program compares the number of peaks that have been found with the number desired. If the number of peaks found matches the number of peaks desired, the peak positions are stored and the search is terminated. If, on the other hand, the number of peaks found is less than the number of peaks desired, the next LEAP2 iteration is performed.

The finding of successive peaks is conducted as follows. The search is started on the incline leading to a peak and the local maximum, MAX1 is set. Then I is incremented, MAX1 is updated for each new ARRAY(I), and a check is performed to determine if a drop such that MAX1−LEAP2>ARRAY(I). This drop signals the decline leading away from a peak whose highest point is MAX1. The height of this current peak is compared to the heights of the two highest previously found peaks, and the latter are updated. A local minimum, MIN1, is set equal to ARRAY(I) where the drop occurs. I is incremented, MIN1 is updated for each new ARRAY(I), and a check is performed to determine if a leap upward such that ARRAY(I)->LEAP2+MIN1. Such a leap indicates the incline leading to the next peak, at which point the above procedure is re-employed. In particular, the interface search begins at I=IUP1 and sets the local maximum equal to ARRAY(IUP1). The above process for finding successive peaks is then used until I reaches IUP2. At this point the program is checked to see how many peaks have been found as described hereinabove.

It is understood that variations and modifications of the present invention can be made without departing from the scope of the invention. It is also to be understood that the scope of the invention is not to be interpreted as limited to the specific embodiments disclosed herein, but only in accordance with the appended claims when read in light of the foregoing disclosure.

What is claimed is:

1. A method for detecting fluid interfaces in a sample, comprising:
   centrifuging said sample; and
   periodically imaging said sample in a plurality of planes during centrifuging.

2. A method as described in claim 1, wherein said imaging comprises illuminating and detecting the position of fluid interfaces in said plurality of planes with electromagnetic energy.

3. A method for collecting and measuring quantities of fluids from a sample, comprising:
   centrifuging said sample to remove at least a portion of said fluids contained therein;
   collecting said fluids in a measuring container during said centrifuging;
   projecting light through said container;
   capturing said light after passage through said container with a photodiode array; and
   periodically measuring the light intensity at each diode of said array to detect the position and movement of fluid interfaces in said container during said centrifuging.

4. The method of claim 3, wherein said centrifuging is conducted at a plurality of preselected speeds.

5. The method of claim 4, further comprising:
adding flotation materials to said container to further define said fluid interfaces.

6. Apparatus for detecting fluid interfaces in a sample, comprising:
a centrifuge having a predetermined number of sample holders and capable of variable speeds of operation;
a source of electromagnetic energy positioned to radiate onto at least one preselected holder as it passes by said source;
a photodiode array positioned to detect electromagnetic energy emanating from said at least one preselected holder;
synchronizing means for preselecting said at least one preselected holder to be irradiated by said source and whose electromagnetic energy is to be detected by said array;
recorder means for recording the signals from said array; and
controller means for controlling the speed of operation of said centrifuge, said synchronizing means, and said recorder means.

7. The apparatus of claim 6, further comprising:
digital computer means for processing said signals from said array and controlling said controller means in functional response to said processed signals.

8. Apparatus for collecting and measuring quantities of fluids in a sample, comprising:
a centrifuge having a predetermined number of sample holders and capable of variable speeds of operation;
a container for collecting fluids from said sample attached to each of said sample holders;
a source of electromagnetic energy positioned to radiate onto at least one preselected container as it passes by said source;
a photodiode array positioned opposite said source to detect electromagnetic energy passing through said at least one preselected container;
synchronizing means for preselecting said at least one preselected container to be irradiated by said source and whose electromagnetic energy is to be detected by said array;
recorder means for recording the signals from said array; and
controller means for controlling the speed of operation of said centrifuge, said synchronizing means, and said recorder means.

9. The apparatus of claim 8, further comprising:
digital computer means for processing said signals from said array and controlling said controller means in functional response to said processed signals.

10. The apparatus of claim 7, wherein said source of electromagnetic energy is a source of light.

11. The apparatus of claim 9, wherein said source of electromagnetic energy is a source of light.

* * * * *